(12) United States Patent
Schweighoffer et al.

(10) Patent No.: US 7,872,015 B2
(45) Date of Patent: Jan. 18, 2011

(54) METHODS INVOLVING PDE4, COMPOSITIONS, AND THE SCREENING THEREOF, FOR THE TREATMENT OF DEGENERATIVE OCULAR PATHOLOGIES

(75) Inventors: Fabien Schweighoffer, Vincennes (FR); Annelies Resink, Laren (NL); Laurent Desire, Paris (FR); Magali Rouquette, Toulouse (FR)

(73) Assignee: Exonhit Therapeutics SA, Paris (FR)

( * ) Notice: Subject to any disclaimer, the term of this patent is extended or adjusted under 35 U.S.C. 154(b) by 1593 days.

(21) Appl. No.: 10/541,503

(22) PCT Filed: Feb. 18, 2004

(86) PCT No.: PCT/FR2004/000366

§ 371 (c)(1), (2), (4) Date: Jul. 7, 2005

(87) PCT Pub. No.: WO2004/073711

PCT Pub. Date: Sep. 2, 2004

(65) Prior Publication Data

US 2006/0241062 A1    Oct. 26, 2006

(30) Foreign Application Priority Data

Feb. 19, 2003  (FR) ................................... 03 02021

(51) Int. Cl.
- *A01N 43/42* (2006.01)
- *A01N 43/40* (2006.01)
- *A01N 43/56* (2006.01)
- *A61K 31/44* (2006.01)
- *A61K 31/415* (2006.01)

(52) U.S. Cl. .................. 514/299; 514/303; 514/341; 514/352; 514/355; 514/407

(58) Field of Classification Search ................. 514/299, 514/303, 341, 352, 355, 407
See application file for complete search history.

(56) References Cited

U.S. PATENT DOCUMENTS

| | | | | |
|---|---|---|---|---|
| 4,904,472 A * | 2/1990 | Belardinelli et al. | ..... | 514/263.1 |
| 6,083,483 A | 7/2000 | Stief et al. | | |
| 6,326,201 B1 * | 12/2001 | Fung et al. | .................. | 435/377 |
| 2002/0119923 A1 | 8/2002 | Benowitz | | |
| 2002/0132826 A1 | 9/2002 | Levin et al. | | |
| 2002/0177599 A1 | 11/2002 | Allerton et al. | | |

FOREIGN PATENT DOCUMENTS

| | | |
|---|---|---|
| EP | 0 583 821 | 2/1994 |
| EP | 1 403 270 | 3/2004 |
| WO | 95/28926 | 11/1995 |
| WO | 98/53856 | 12/1998 |
| WO | 00/15222 | 3/2000 |
| WO | 01/49321 | 7/2001 |
| WO | WO01/049321 | * 7/2001 |
| WO | 01/58469 | 8/2001 |
| WO | 01/81348 | 11/2001 |
| WO | 02/051502 | 7/2002 |
| WO | 02/098878 | 12/2002 |
| WO | 03/016563 | 2/2003 |
| WO | 03/045949 | 6/2003 |
| WO | 03/099278 | 12/2003 |
| WO | 2004/011464 | 2/2004 |
| WO | 2004/024085 | 3/2004 |

OTHER PUBLICATIONS

Cavalia et al (Current Medicinal Chemistry 2 (1995) 561-572).*
Amabati et al (Survey Of Ophthalmology vol. 48, No. 3 (2003) pp. 257-293).*
International Search Report for PCT/FR2004/000366 dated Jan. 14, 2005.
Database WPI Week 200315, Dec. 19, 2002, Derwent Publications Ltd., AN: 2003-156939, XP002294573; Aotsuka et al. & WO 02/100859.
Database WPI Week 199641, Aug. 6, 1996, Derwent Publications Ltd., AN: 1996-408420, XP002266210; JP19950012463, Yoshitomi Pharm Ind KK.
Beatty S et al. (Surv Ophthalmol. Sep.-Oct. 2000;45(2):115-34 "The role of oxidative stress in the pathogenesis of age-related macular degeneration." (Abstract).
Hubschman JP et al, Clin Ophthalmol. 2009;3:167-74 "Age-related macular degeneration: current treatments".
Marcade et al, J Neurochem. Jul. 2008;106(1):392-404 "Etazolate, a neuroprotective drug linking GABA(A) receptor pharmacology to amyloid precursor protein processing" (Abstract).

* cited by examiner

*Primary Examiner*—Frederick Krass
*Assistant Examiner*—Benjamin Packard
(74) *Attorney, Agent, or Firm*—Nixon & Vanderhye P.C.

(57) ABSTRACT

The invention relates to the field of biology, genetics and medicine. In particular, the invention relates to novel methods for the detection, characterization and/or treatment (or management) of neurodegenerative pathologies. The invention also relates to methods for the identification or screening of compounds active in the aforementioned pathologies. The invention further relates to the compounds, genes, cells, plasmids or compositions which are used to carry out said methods. In particular, the invention is based on the identification of the role of phosphodiesterase 4B, the peripheral benzodiazepine receptor (PBR) and GABA receptors of the type GABA(A) in neurodegenerative pathologies and describes the use of same as therapeutic, diagnostic or experimental markers or targets for said disorders.

3 Claims, 8 Drawing Sheets

Figure 1A:
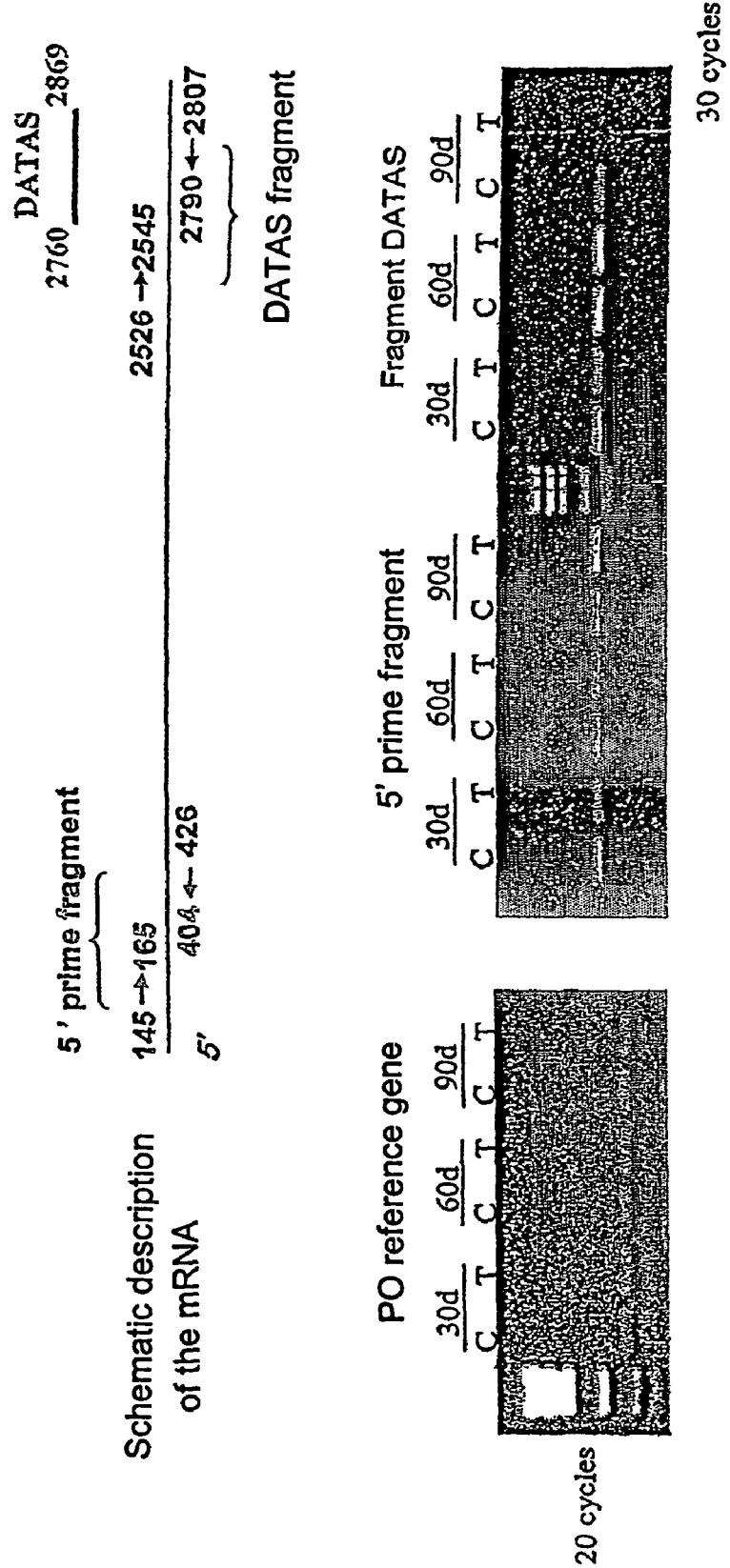

SEQUENCE LISTING

```
<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
gccaggccgt gaagcaaata                                               20
```

-continued

```
<210> SEQ ID NO 2
<211> LENGTH: 18
<212> TYPE: DNA
<213> ORGANISM: artificial sequence
<220> FEATURE:
<223> OTHER INFORMATION: primer

<400> SEQUENCE: 2
tcaaagacgc gaaaacat                                              18

<210> SEQ ID NO 3
<211> LENGTH: 21
<212> TYPE: DNA
<213> ORGANISM: artificial sequence
<220> FEATURE:
<223> OTHER INFORMATION: primer

<400> SEQUENCE: 3
ccgcgtcagt gcctttgcta t                                          21

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4
cgctgtcgga tgcttttatt cac                                        23

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
tcgctttctg gagggtgtc                                             19

<210> SEQ ID NO 6
<211> LENGTH: 18
<212> TYPE: DNA
<213> ORGANISM: artificial sequence
<220> FEATURE:
<223> OTHER INFORMATION: primer

<400> SEQUENCE: 6
ccgcaggggc agcagtgg                                              18
```

METHODS INVOLVING PDE4, COMPOSITIONS, AND THE SCREENING THEREOF, FOR THE TREATMENT OF DEGENERATIVE OCULAR PATHOLOGIES

This application is the US national phase of international application PCT/FR2004/000366 filed 18 Feb. 2004, which designated the U.S. and claims benefit of FR 03 02021, filed 19 Feb. 2003, the entire contents of each of which are hereby incorporated by reference.

The invention relates to the field of biology, genetics and medicine. In particular, the invention relates to novel methods for the detection, characterization and/or treatment (or management) of neurodegenerative pathologies. The invention also relates to methods for the identification or screening of compounds active in the aforementioned pathologies. The invention further relates to the compounds, genes, cells, plasmids or compositions which are used to carry out said methods. In particular, the invention is based on the identification of the role of phosphodiesterase 4B and the peripheral benzodiazepine receptor in neurodegenerative ocular pathologies and describes the use of same as therapeutic, diagnostic or experimental markers or targets for said disorders.

Many neurodegenerative pathologies have been described as having a component or a stage related to the phenomenon of apoptosis or programmed cell death. Examples include both neurodegenerative diseases of the central nervous system (for example amyotrophic lateral sclerosis (ALS), Parkinson's disease or Alzheimer's disease) and peripheral degenerative diseases, particularly ocular. Symptomatic treatments currently exist for such pathologies, particularly treatment of associated inflammatory phenomena, but there are no treatments for the causes of these disorders, due in particular to the complexity of the underlying mechanisms and metabolic pathways, and the diversity of causal factors.

Application WO03/045949 describes GSK3 inhibitors which can be used in neurodegenerative diseases. Applications WO01/49321 and WO01/58469 propose the use of TNH inhibitor compounds to treat neurologic pathologies. Application WO00/15222 describes using PDE5 inhibitors in the treatment of erectile dysfunction. Application EP583821 provides therapeutic approaches for treating deregulations of cranial fluid volume.

International patent application PCT/FR02/02861 filed by the applicant describes novel molecular targets of neurotoxicity, and novel therapeutic approaches for the treatment of neurodegenerative pathologies. Said approaches are based on modulating the activity or expression of a phosphodiesterase type 4, and on modifying the regulation of the peripheral benzodiazepine receptor and the GABA(A) receptor.

The present application now relates to novel therapeutic strategies for neurodegenerative ocular diseases. Said strategies are based on modulating one or more metabolic pathways identified by the inventors, which are correlated with the onset, development and progression of excitotoxicity and apoptosis in nerve cells, and are particularly pertinent in neurodegenerative ocular diseases.

More particularly, a repertoire of RNA splicing alterations in brain and spinal cord of animals in an ALS model, aged 60 days, has been identified by qualitative differential screening according to the DATAS method (described in application WO99/46403). This repertoire was constructed from RNA extracted from brain and spinal cord samples, without preliminary isolation of neurons, so as to take into account a maximum of alternative splicing events related to disease development. The repertoire so produced contains more than 200 separate sequences, involving key components in the excitotoxicity phenomenon, such as potassium and calcium channels. The specificity of the sequences in this repertoire is confirmed by the fact that the same qualitative differential analysis of genetic expression performed on 90-day-old animals led to a different repertoire wherein, in particular, the different markers of excitotoxicity are absent. Analysis of the splicing modifications confirms that the molecular events differ according to the stage of disease In a particularly noteworthy and unexpected manner, the use of DATAS on RNA from 60-day-old control and transgenic animals led to the isolation of cDNA fragments derived from the mRNA for phosphodiesterase 4B, protein AKAP1 (A Kinase Anchoring Protein) and protein GABA(A)RAPL1 (GABA(A) Receptor Associated Protein Like 1). The PDE4B protein, capable of hydrolysing cAMP, is involved in regulating intracellular cAMP concentrations. The AKAP1 protein anchors the regulatory subunit of protein kinase A (activated by cAMP) to the mitochondrial membrane and regulates the activity of the mitochondrial transition pore through its interaction with the peripheral benzodiazepine receptor (PBR).

The application thereby demonstrates the involvement of cAMP-dependent signalling cascades, PBR regulation and GABA(A) receptor-dependent signalling in the development of excitotoxic processes and neuron death.

More specifically, the results obtained show a higher level of expression of PDE4B in pathological nerve tissues, related to a structural modification of the corresponding RNA, in particular to the deletion of a region in the 3' non-coding region. This finding is altogether compatible with the presence of mRNA destabilization sequences in the sequence identified by DATAS. Deletion of said destabilization sequences from PDE4B mRNA, by splicing or by the use of alternative polyadenylation sequences, can result in a stabilization, therefore in an increase in the expression, of the coding portion of this RNA. Said event occurs specifically in the brain of pathological subjects and not in control subjects.

In addition, the identification of a fragment derived from AKAP1 demonstrates the involvement of this protein in the development of excitotoxic processes and neuron death. AKAP1 interacts with the regulatory subunit of protein kinase A and with the peripheral benzodiazepine receptor (PBR), which plays a role in regulating the opening of the mitochondrial transition pore, said opening characterizing the implementation of apoptosis. Consequently, the invention suggests that AKAP1 regulates the participation of the PBR in cell death phenomena such as death of neurons.

The identification of a fragment derived from GABA(A) RAPL1 highlights a deregulation of GABA(A) receptor-dependent signalling. This observation is altogether compatible with the importance of the neurotransmitter as an inhibitor of synaptic transmission, particularly through its interaction with the GABA(A) receptor. Said inhibition allows neurons to be protected against a sustained excitation which might lead to neuron death from excitotoxicity. Our studies therefore indicate an alteration in this level of regulation.

Thus, the invention outlines three original molecular events characterized by an alteration in the expression of the mRNA for PDE4, AKAP1 and GABA(A)RAPL1 in the brain of pathological subjects, and which are correlated over time with the phenomenon of excitotoxicity and/or neuron death. These signalling pathways, mediated by cAMP, regulating the PBR, and transmitting GABA-dependent signals, define novel strategies for the development of therapies for neurodegenerative diseases, which can be used in particular in the early phases of disease, and which are aimed at the actual molecular bases of the pathology- and not at the symptoms or associated inflammatory phenomena.

The opportunity to act on one or, preferably, on these three metabolic pathways simultaneously would thus lead to particularly effective treatments for neurodegenerative diseases, in particular ocular. In fact, it is known that retinal neurodegeneration (and particularly the loss of photoreceptors) is associated with variations in retinal levels of cyclic nucleotides (cGMP, cAMP). Modulation of said levels might therefore be beneficial in the treatment of neurodegenerative ocular diseases, in particular by controlling excitotoxicity.

A first aspect of the invention therefore relates to the use of a PBR ligand for preparing a pharmaceutical composition intended for the treatment of neurodegenerative pathologies, in particular neurodegenerative ocular pathologies.

Another aspect of the invention is based on the use of a PDE4 inhibitor compound for preparing a pharmaceutical composition intended for the treatment of neurodegenerative ocular diseases.

A third aspect of the invention is based on the use of a compound which regulates the activity of GABA(A) receptors for preparing a pharmaceutical composition intended for the treatment of neurodegenerative ocular diseases.

A more particular object of the invention relates to the use of a PDE4 inhibitor compound belonging to the pyrazolopyridine family for preparing a pharmaceutical composition intended to increase neuron survival in patients with neurodegenerative ocular diseases.

Another object of the invention concerns the use of a PDE4 inhibitor compound belonging to the pyrazolopyridine family for preparing a pharmaceutical composition intended to inhibit or reduce neuron death due to excitotoxicity during neurodegenerative ocular diseases.

In a preferred manner, the PDE4 inhibitor compound is also a ligand of the peripheral benzodiazepine receptor (PBR) and/or a ligand of the beta subunits of GABA(A) receptors. In fact, such compounds advantageously make it possible to act on three metabolic pathways involved in neurodegenerative diseases. A particularly preferred compound is etazolate.

In another embodiment, three compounds are used in combination, one being a PDE4 inhibitor, a second being a GABA(A) receptor ligand, the other a ligand of the peripheral benzodiazepine receptor (PBR). The combined use can be simultaneous, separate or spread out over time.

In a further embodiment, the compound is an antisense nucleic acid capable of inhibiting the transcription of the PDE4B, AKAP1 or GABA(A)RAPL1 gene, or the translation of the corresponding messenger mRNA.

The invention is particularly adapted to the treatment of degenerative processes of the retina and in particular to the treatment of retinitis pigmentosa, macular degeneration, the retinal effects of glaucoma or diabetic retinopathies.

The invention also provides for the development of tests, kits or methods for the detection, screening or in vitro diagnosis of said pathologies, based on determining the presence of a deregulation or an alteration in a gene, messenger or protein coding for PDE4 or AKAP1, or else GABA(A)RAPL1, in a subject. The invention also provides tools for implementing said tests, particularly probes, primers, cells, reagents and the like.

The invention also provides tests or methods for screening candidate molecules for the treatment of neurodegenerative diseases, comprising determining the capacity of molecules to bind to the receptor PBR, AKAP1, GABA(A)RAPL1, the GABA(A) receptor and/or PDE4.

Another object of the invention concerns a pharmaceutical composition comprising a compound from the pyrazolopyridine family and a pharmaceutically acceptable excipient and which is adapted to extra- or intra-ocular administration. Preferably, the compound is such as defined hereinabove, in particular it is etazolate. Typically, the composition is formulated as an injectable solution, a collyrium, gel, drops, and the like.

Therapy

Thus, the present invention generally relates to the use of PDE4 inhibitors and/or ligands of PBR and GABA(A) for the treatment of neurodegenerative ocular diseases.

The use of PDE4 inhibitors has never been envisioned for improving neuron viability and more particularly for protecting neurons against excitotoxicity. PDE4 inhibitors, which were developed to inhibit inflammatory phenomena, have been suggested as being potentially useful in central neurodegenerative pathologies such as Alzheimer's disease. This suggestion is based on the goal of reducing the inflammation observed in the brain during neurodegenerative processes and not at all on a rationale aiming to directly inhibit neuron death. Moreover, this suggestion in no way relates to peripheral diseases, particularly ocular.

The invention demonstrates the existence of alternative polyadenylation sites or splicing events affecting the genes encoding PDE4 and AKAP1 and GABA(A)RAPL1, associated with the development of neuronal excitotoxicity, and provides the molecular basis which justifies the use of PDE4 inhibitors and/or PBR and GABA(A) receptor ligands for treating neurodegenerative ocular diseases and more generally for improving neuron viability during excitotoxic phenomena, in particular right from the early phases of said pathologies.

One object of the invention is therefore based on the use of a PDE4 inhibitor compound and/or a PBR and GABA(A) receptor ligand for preparing a pharmaceutical composition intended for the treatment of neurodegenerative ocular diseases, in particular to promote or favor neuron survival in afflicted patients.

In a preferred manner, the PDE4 inhibitor compound is also a ligand of the peripheral benzodiazepine receptor (PBR) and the GABA(A) receptor. In fact, said compounds allow to act advantageously on three metabolic pathways involved in neurodegenerative diseases.

In another embodiment, three compounds are used in combination, one being a PDE4 inhibitor, the second a peripheral benzodiazepine receptor (PBR) ligand and the third a ligand of the GABA(A) receptor. The combined use can be simultaneous, separate or spread out over time.

Another object of the invention is based on a method of treatment of a neurodegenerative ocular pathology, comprising administering to a subject a PDE4 inhibitor compound and/or PBR and GABA(A) receptor ligand, preferably a PDE4 inhibitor compound and ligand of the PBR and GABA(A) receptor.

A further object of the invention is based on a method for increasing neuron survival in patients afflicted with a neurodegenerative ocular disease, comprising administering to a subject a compound such as defined hereinabove.

A further object of the invention is based on the use of a compound such as defined hereinabove for inhibiting or reducing neuronal excitotoxicity during neurodegenerative ocular diseases, that is, more particularly for inhibiting or reducing neuron death due to excitotoxicity during neurodegenerative ocular diseases.

Another aspect of the invention concerns the use of at least one PDE4 inhibitor compound belonging to the pyrazolopyridine family, for preparing a pharmaceutical composition intended to increase neuron survival in patients with neurodegenerative ocular diseases.

In the spirit of the invention, the term "treatment" denotes preventive, curative, palliative treatment as well as management of patients (alleviating suffering, reducing functional deficit, improving survival, slowing disease progression, improving neuron survival, protecting neurons against excitotoxicity or apoptosis, etc.). The treatment can furthermore be carried out in combination with other agents or treatments, in particular participating in the late events of the pathology, such as caspase inhibitors or other active compounds.

The term "PDE4 inhibitor compound" designates any compound capable of inhibiting the expression or activity of PDE4, particularly PDE4B, that is to say, in particular, any compound inhibiting the transcription of the gene, the maturation of RNA, the translation of mRNA, the posttranslational modification of the protein, the enzymatic activity of the protein, the interaction of same with a substrate, etc. It can be a compound inhibiting the modification of RNA, particularly the deletion of part of the 3' non-coding region.

In a particular embodiment, the comopund is an antisense nucleic acid, capable of inhibiting the transcription of the PDE4B or AKAP1 or GABA(A)RAPL1 gene or the translation of the corresponding messenger. The antisense nucleic acid can comprise all or part of the sequence of the PDE4B or AKAP1 or GABA(A)RAPL1 gene, a fragment thereof, the PDE4B or AKAP1 or GABA(A)RAPL1 messenger, or a sequence complementary to same. In particular, the antisense molecule can comprise a region complementary to the sequence comprised between residues 218-2383 of Genbank sequence No. AF208023 or 766-2460 of Genbank sequence No. NM_002600, and inhibit (or reduce) the translation thereof into protein. The antisense molecule can be a DNA, RNA, ribozyme, etc. It can be single stranded or double stranded. It can also be an RNA coded by an antisense gene. It being an antisense oligonucleotide, it typically comprises fewer than 100 bases, for example approximately 10 to 50 bases. Said oligonucleotide can be modified to improve its stability, its resistance to nucleases, its penetration into the cell, etc.

According to another embodiment, the compound is a peptide, for example comprising a region of the PDE4 (in particular PDE4B) protein and capable of antagonizing the activity of same.

According to another embodiment, the compound is a chemical compound, natural or synthetic, in particular an organic or inorganic molecule of plant, bacterial, viral, animal, eukaryotic, synthetic or semisynthetic origin, capable of modulating the expression or activity of PDE4B, and/or of binding to the PBR receptor and/or a GABA receptor of the type GABA(A)

In a preferred variant, a compound from the pyrazolopyridine family is used, in particular such as etazolate. In fact, said compounds are capable of binding to the PBR and GABA(A) receptors and inhibiting PDE4.

Compounds from the pyrazolopyridine family are selected in particular in the group consisting of the following compounds:

Etazolate which has the following formula:

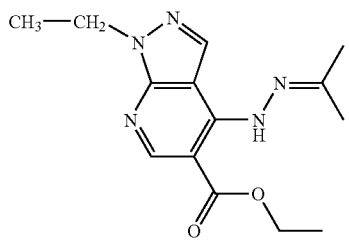

etazolate representing a preferred embodiment of the invention, 4-butylamino-1-ethyl-6-methyl-1H-pyrazolo[3,4-b]pyridine-5-carboxylic acid ethyl ester (tracazolate),
4-butylamino-1-ethyl-1H-pyrazolo[3,4-b]pyridine-5-carboxylic acid ethyl ester,
1-(4-amino-pyrazolo[3,4-b]pyridin-1-yl)-β-D-1-deoxy-ribofuranose,
1-ethyl-4-(N'-isopropylidene-hydrazino)-1H-pyrazolo[3,4-b]pyridine-5-carboxylic acid ethyl ester (SQ 20009),
4-amino-6-methyl-1-n-pentyl-1H-pyrazolo[3,4-b]pyridine,
4-amino-1-ethyl-6-methyl-1H-pyrazolo[3,4-b]pyridine-5-carboxylic acid ethyl ester (desbutyl tracacolate),
4-amino-1-pentyl-1H-pyrazolo[3,4-b]pyridine-5-carboxamide,
1-ethyl-6-methyl-4-methylamino-1H-pyrazolo[3,4-b]pyridine-5-carboxylic acid ethyl ester,
4-amino-6-methyl-1-propyl-1H-pyrazolo[3,4-b]pyridine-5-carboxylic acid ethyl ester,
1-ethyl-4-ethylamino-6-methyl-1H-pyrazolo[3,4-b]pyridine-5-carboxylic acid ethyl ester,
4-amino-1-butyl-6-methyl-1H-pyrazolo[3,4-b]pyridine-5-carboxylic acid ethyl ester,
5-(4-amino-pyrazolo[3,4-b]pyridin-1-yl)-2-hydroxymethyl-tetrahydro-furan-3-ol,
1-allyl-4-amino-6-methyl-1H-pyrazolo[3,4-b]pyridine-5-carboxylic acid allyl ester,
4-amino-6-methyl-1-pentyl-1H-pyrazolo[3,4-b]pyridine-5-carboxylic acid,
4-amino-1-ethyl-3,6-dimethyl-1H-pyrazolo[3,4-b]pyridine-5-carboxylic acid ethyl ester,
4-dimethylamino-1-ethyl-6-methyl-1H-pyrazolo[3,4-b]pyridine-5-carboxylic acid ethyl ester,
1-ethyl-6-methyl-4-propylamino-1H-pyrazolo[3,4-b]pyridine-5-carboxylic acid ethyl ester,
4-amino-1-pentyl-1H-pyrazolo[3,4-b]pyridine-5-carboxylic acid ethyl ester,
4-amino-6-methyl-1-pent-4-ynyl-1H-pyrazolo[3,4-b]pyridine-5-carboxylic acid ethyl ester,
4-amino-1-but-3-enyl-1H-pyrazolo[3,4-b]pyridine-5-allylamide,
4-amino-1-pentyl-1H-pyrazolo[3,4-b]pyridine-5-isopropylamide,
4-amino-1-pentyl-N-n-propyl-1H-pyrazolo-[3,4-b]pyridine-5-carboxamide,
4-amino-1-butyl-6-methyl-1H-pyrazolo[3,4-b]pyridine-5-carboxylic acid allyl ester,
4-amino-6-methyl-1-pent-3-ynyl-1H-pyrazolo[3,4-b]pyridine-5-carboxylic acid ethyl ester,
4-amino-1-pentyl-1H-pyrazolo[3,4-b]pyridine-5-prop-2-ynylamide,
4-amino-1-(3-methyl-butyl)-1H-pyrazolo[3,4-b]pyridine-5-carboxylic acid allyl ester,
4-amino-1-pentyl-1H-pyrazolo<3,4-b>pyridine-5-N-(2-propenyl)carboxamide,
4-amino-1-pentyl-1H-pyrazolo[3,4-b]pyridine-5-carboxylic acid allyl ester,
4-amino-1-pentyl-1H-pyrazolo[3,4-b]pyridine-5-butylamide,
4-amino-1-but-3-ynyl-6-methyl-1H-pyrazolo[3,4-b]pyridine-5-carboxylic acid allyl ester,
4-amino-1-but-3-enyl-6-methyl-1H-pyrazolo[3,4-b]pyridine-5-carboxylic acid allyl ester,
4-amino-6-methyl-1-pentyl-1H-pyrazolo[3,4-b]pyridine-5-allylamide,
4-amino-6-methyl-1-pentyl-1H-pyrazolo[3,4-b]pyridine-5-carboxylic acid allyl ester, 4-amino-6-methyl-1-(3-methyl-butyl)-1H-pyrazolo[3,4-b]pyridine-5-carboxylic acid allyl ester,
4-amino-6-methyl-1-pentyl-1H-pyrazolo[3,4-b]pyridine-5-carboxylic acid isobutyl ester,
4-amino-6-methyl-1-pentyl-1H-pyrazolo[3,4-b]pyridine-5-butylamide,
4-amino-6-methyl-1-(3-methyl-but-2-enyl)-1H-pyrazolo[3,4-b]pyridine-5-carboxylic acid allyl ester,
4-amino-1-pentyl-1H-pyrazolo[3,4-b]pyridine-5-cyclopropylamide,
ethyl 4-amino-1-pentyl-1H-pyrazolo[3,4-b]pyridine-5-hydroxamate,
4-amino-6-methyl-1-pentyl-1H-pyrazolo[3,4-b]pyridine-5-carboxylic acid prop-2-ynyl ester,
4-amino-6-methyl-1-pent-4-ynyl-1H-pyrazolo[3,4-b]pyridine-5-carboxylic acid allyl ester,
4-amino-6-methyl-1-pent-4-enyl-1H-pyrazolo[3,4-b]pyridine-5-carboxylic acid allyl ester,
4-amino-1-pent-3-ynyl-1H-pyrazolo[3,4-b]pyridine-5-propylamide,
4-amino-1-pentyl-1H-pyrazolo[3,4-b]pyridine-5-cyclopropylmethyl-amide,
4-amino-6-methyl-1-pentyl-1H-pyrazolo[3,4-b]pyridine-5-carboxylic acid 2-methylallyl ester,
4-amino-1-pent-3-ynyl-1H-pyrazolo[3,4-b]pyridine-5-allylamide (ICI 190,622),
4-amino-1-pent-4-ynyl-N-2-propenyl-1H-pyrazolo[3,4-b]pyridine-5-carboxamide,
4-amino-1-pent-3-ynyl-1H-pyrazolo[3,4-b]pyridine-5-prop-2-ynylamide,
4-amino-1-pentyl-1H-pyrazolo[3,4-b]pyridine-5-but-2-ynylamide,
4-amino-6-methyl-1-pent-3-ynyl-1H-pyrazolo[3,4-b]pyridine-5-carboxylic acid allyl ester,
4-amino-1-(2-cyclopropyl-ethyl)-6-methyl-1H-pyrazolo[3,4-b]pyridine-5-carboxylic acid allyl ester,
4-amino-1-hex-5-ynyl-6-methyl-1H-pyrazolo[3,4-b]pyridine-5-carboxylic acid allyl ester,
4-amino-1-pent-3-ynyl-1H-pyrazolo[3,4-b]pyridine-5-cyclopropylmethyl-amide,
4-amino-6-methyl-1-pentyl-1H-pyrazolo[3,4-b]pyridine-5-carboxylic acid but-3-enyl ester,
4-amino-6-methyl-1-pentyl-1H-pyrazolo[3,4-b]pyridine-5-carboxylic acid cyclopropylmethyl ester,
4-butylamino-1-pentyl-1H-pyrazolo[3,4-b]pyridine-5-allylamide,
4-amino-6-methyl-1-pentyl-1H-pyrazolo[3,4-b]pyridine-5-carboxylic acid 2-cyclopropyl-ethyl ester,
4-amino-6-methyl-1-pent-3-ynyl-1H-pyrazolo[3,4-b]pyridine-5-carboxylic acid cyclopropylmethyl ester,
4-amino-6-methyl-1-pent-4-ynyl-1H-pyrazolo[3,4-b]pyridine-5-carboxylic acid cyclopropylmethyl ester,
4-amino-1-benzyl-6-methyl-1H-pyrazolo[3,4-b]pyridine-5-carboxylic acid ethyl ester,
4-amino-1-pentyl-1H-pyrazolo[3,4-b]pyridine-5-benzylamide,
4-amino-1-pentyl-1H-pyrazolo[3,4-b]pyridine-5-phenylamide,
4-amino-6-methyl-1-pentyl-1H-pyrazolo[3,4-b]pyridine-5-carboxylic acid benzyl ester,
4-azido-1-β-D-ribofuranosylpyrazolo[3,4-b]pyridine,
1-pent-3-ynyl-N-2-propenyl-4-propionamido-1H-pyrazolo[3,4-b]pyridine-5-carboxamide,
2-(4-amino-pyrazolo[3,4-b]pyridin-1-yl)-5-hydroxymethyl-tetrahydro-furan-3,4-diol,
2-(6-methyl-1H-pyrazolo[3,4-b]pyridin-4-ylamino)-ethanol,
3-(6-methyl-1H-pyrazolo[3,4-b]pyridin-4-ylamino)-propan-1-ol,
3-(6-methyl-1H-pyrazolo[3,4-b]pyridin-4-ylamino)-acetic acid propyl ester,
2-(6-methyl-1H-pyrazolo[3,4-b]pyridin-4-ylamino)-propionic acid ethyl ester,
2-(6-methyl-1H-pyrazolo[3,4-b]pyridin-4-ylamino)-pentanoic acid ethyl ester,
2-(6-methyl-1H-pyrazolo[3,4-b]pyridin-4-ylamino)-benzoic acid ethyl ester,
3-(6-methyl-1H-pyrazolo[3,4-b]pyridin-4-ylamino)-pentanoic acid propyl ester,
N-benzylidene-N'-(3-methyl-1-phenyl-1H-pyrazolo[3,4-b]pyridin-4-yl)-hydrazine,
N-furan-2-ylmethylene-N'-(3-methyl-1-phenyl-1H-pyrazolo[3,4-b]pyridin-4-yl)-hydrazine,
N-(4-fluoro-benzylidene)-N'-(3-methyl-1-phenyl-1H-pyrazolo[3,4-b]pyridin-4-yl)-hydrazine,
N-(3-furan-2-yl-allylidene)-N'-(3-methyl-1-phenyl-1H-pyrazolo[3,4-b]pyridin-4-yl)-hydrazine,
N-(4-methoxy-benzylidene)-N'-(3-methyl-1-phenyl-1H-pyrazolo[3,4-b]pyridin-4-yl)-hydrazine,
4-[(3-methyl-1-phenyl-1H-pyrazolo[3,4-b]pyridin-4-yl)-hydrazonomethyl]-benzonitrile,
N-benzo[1,3]dioxol-5-ylmethylene-N'-(3-methyl-1-phenyl-1H-pyrazolo[3,4-b]pyridin-4-yl)-hydrazine,
N-(3-methyl-1-phenyl-1H-pyrazolo[3,4-b]pyridin-4-yl)-N'-(4-nitro-benzylidene)-hydrazine,
N-(3-methyl-1-phenyl-1H-pyrazolo[3,4-b]pyridin-4-yl)-N'-(2-nitro-benzylidene)-hydrazine,
N-(3-methyl-1-phenyl-1H-pyrazolo[3,4-b]pyridin-4-yl)-N'-(4-trifluoromethyl-benzylidene)-hydrazine,
N-(3-methyl-1-phenyl-1H-pyrazolo[3,4-b]pyridin-4-yl)-N'-(5-nitro-furan-2-ylmethylene)-hydrazine,
N-(3-methyl-1-phenyl-1H-pyrazolo[3,4-b]pyridin-4-yl)-N'-(2-trifluoromethyl-benzylidene)-hydrazine,
N-(3-methyl-1-phenyl-1H-pyrazolo[3,4-b]pyridin-4-yl)-N'-(6-nitro-benzo[1,3]dioxol-5-ylmethylene)-hydrazine,
4-(3-chloro-4-methoxy-benzylamino)-1-ethyl-1H-pyrazolo[3,4-b]pyridine-5-carboxylic acid,
4-(3-chloro-4-methoxy-benzylamino)-1-ethyl-1H-pyrazolo[3,4-b]pyridine-5-(pyridin-4-ylmethyl)-amide,
4-(3-chloro-4-methoxy-benzylamino)-1-ethyl-1H-pyrazolo[3,4-b]pyridine-5-(tetrahydro-furan-2-yl methyl)-amide,
4-(3-chloro-4-methoxy-benzylamino)-1-ethyl-1H-pyrazolo[3,4-b]pyridine-5-(5-hydroxy-pentyl)-amide,
4-(3-chloro-4-methoxy-benzylamino)-1-ethyl-1H-pyrazolo[3,4-b]pyridine-5-[3-(2-oxo-pyrrolidin-1-yl)-propyl]-amide,
4-tert-butylamino-1-(2-chloro-2-phenyl-ethyl)-1H-pyrazolo[3,4-b]pyridine-5-carboxylic acid ethyl ester,
1-(2-chloro-2-phenyl-ethyl)-4-cyclopropylamino-1H-pyrazolo[3,4-b]pyridine-5-carboxylic acid ethyl ester,
1-(2-chloro-2-phenyl-ethyl)-4-propylamino-1H-pyrazolo[3,4-b]pyridine-5-carboxylic acid ethyl ester,
1-(2-chloro-2-phenyl-ethyl)-4-phenylamino-1H-pyrazolo[3,4-b]pyridine-5-carboxylic acid ethyl ester,
4-butylamino-1-(2-chloro-2-phenyl-ethyl)-1H-pyrazolo[3,4-b]pyridine-5-carboxylic acid ethyl ester,
1-(2-chloro-2-phenyl-ethyl)-4-(2-ethoxy-ethylamino)-1H-pyrazolo[3,4-b]pyridine-5-carboxylic acid ethyl ester,
4-benzylamino-1-(2-chloro-2-phenyl-ethyl)-1H-pyrazolo[3,4-b]pyridine-5-carboxylic acid ethyl ester, 1-(2-chloro-2-phenyl-ethyl)-4-phenethylamino-1H-pyrazolo[3,4-b]pyridine-5-carboxylic acid ethyl ester.

The invention reveals that said compounds have the unequalled interest of being able to interfere with three molecular events involved in regulating cell life. On the one hand, they maintain intracellular cAMP concentrations at a level which prevents activation of cell death apoptotic cascades, and on the other hand they interfere with the actual carrying out of apoptosis by inhibiting the opening of the mitochondrial transition pore. In addition, they are capable of regulating the activity of GABA(A) receptors and therefore of regulating the electrophysiologic activity (polarization) of neurons, thereby protecting the latter against excitotoxicity.

Another property of said compounds is the preferential inhibition, among the phosphodiesterases, of cAMP-dependent phosphodiesterases, that is, which hydrolyze intracellular cAMP. Consequently, said compounds do not affect cGMP concentrations. Increasing the concentration is advantageous when one wants to maintain the viability of neurons such as motor neurons. On the other hand, the cells of the retina, such as rods, suffer from an excess of cGMP, increasing cAMP being less critical.

Therefore, the pyrazolopyridines are particularly adapted to the treatment of retinal degeneration, which is characteristic of retinitis pigmentosa, age-related macular degeneration (ARMD), the effects of glaucoma, and retinopathies, in particular diabetic.

Thus, for the first time, the present invention proposes PDE4, PBR and GABA(A) receptors as therapeutic targets, preferably in combination, for the treatment of molecular events associated with excitotoxicity, particularly in neurodegenerative ocular diseases. According to particular embodiments, the invention can be used to inhibit or reduce neuronal excitotoxicity in the early phase of said diseases. In particular, it can be used for treating the effects of glaucoma on the retina, including open-angle glaucoma and angle-closure glaucoma, age-related macular degeneration (ARMD), diabetic retinopathies and retinitis pigmentosa.

Other examples of ocular pathologies comprise, in particular, the retinal effects of intraocular hypertension, retinal maculopathies and degeneration such as age-related macular degeneration (ARMD) in both the exudative and atrophic ("dry") forms, choroid neovascularization, diabetic retinopathy, central serous chorioretinopathy, cystoid macular oedema, diabetic macular oedema, myopic retinal degeneration; infections (syphilis, Lyme's disease, tuberculosis, toxoplasmosis); inflammatory diseases of the eye, such as acute multifocal placoid pigment epitheliopathy, Behçet's disease, birdshot retinochoroidopathy, uveitis (anterior, posterior, panuveitis), multifocal choroiditis, Multiple Evanescent White Dot Syndrome (MEWDS), ocular sarcoidosis, posterior scleritis, serpiginous choroiditis, subretinal fibrosis, Vogt-Koyanagi-Harada syndrome, punctate choroidopathy, acute macular neuroretinopathy, vascular and exudative diseases such as diabetic retinopathy, occlusion of the central retinal artery and/or its branches, central retinal vein occlusion, disseminated intravascular coagulation, hypertension-related changes in the optic fundus, ocular ischemic syndrome, retinal arterial microaneurysms, retinal injuries, retinal detachment, macular holes, retinal tumors such as congenital hypertrophy of the retinal pigment epithelium, choroidal hemangiomas, choroidal osteomas, choroidal metastases, retinoblastoma, hamartoma, vasculoprolifèrative tumors of the optic fundus, retinal astrocytoma, lymphoid tumors of the retina; genetic diseases of the retina such as retinitis pigmentosa, rod-cone dystrophy, Stargardt's disease and Fundus Flavimaculatus.

A particularly preferred object of the invention is based on the use of etazolate for preparing a pharmaceutical composition intended for the treatment of neurodegenerative ocular diseases.

A particularly preferred object of the invention is based on the use of etazolate for preparing a pharmaceutical composition intended to increase neuron survival in patients with neurodegenerative ocular diseases.

A particularly preferred object of the invention is based on the use of etazolate for preparing a pharmaceutical composition intended to inhibit or reduce neuronal excitotoxicity in patients with neurodegenerative ocular diseases.

The neurodegenerative ocular disease is preferably retinitis pigmentosa, age-related macular degeneration (ARMD), the retinal effects of glaucoma (that is, in particular, the degeneration or death of retinal nerve cells) or a retinopathy.

The compounds can be formulated and administered in different ways. Administration can be carried out by any method known to those skilled in the art, preferably by the oral route or by systemic, local or locoregional injection. Typically, injection is performed by the intra-ocular, retroocular, intraperitoneal, intracerebroventricular, intraspinal, intravenous, intra-arterial, subcutaneous or intramuscular route. Administration by the oral, systemic or retro- or intraocular route is preferred. The administered doses can be adjusted by those skilled in the art. Typically, approximately 0.01 mg to 100 mg/kg are adminstered, for inhibitor compounds of a chemical nature. It is understood that repeated administrations may be given, possibly in combination with other active agents or any pharmaceutically acceptable vehicle or excipient (for example, buffers, saline, isotonic solutions, in the presence of stabilizers, etc.).

The pharmaceutically acceptable vehicle or excipient can be selected in the group consisting of buffer solutions, solvents, binders, stabilizers, emulsifiers and the like. Buffer solutions or diluents include in particular calcium phosphate, calcium sulfate, lactose, cellulose, kaolin, mannitol, sodium chloride, starch, powdered sugar and hydroxy propyl methyl cellulose (HPMC) (for delayed release). Binders are exemplified by starch, gelatin and filler solutions like sucrose, glucose, dextrose, lactose, and the like. Natural or synthetic gums can also be used, such as in particular alginate, carboxymethylcellulose, methylcellulose, polyvinyl pyrrolidone, and the like. Other excipients are exemplified by cellulose and magnesium stearate. Stabilizing agents can be included in the formulations, such as polysaccharides for example (acacia, agar, alginic acid, gum guar and tragacanth, chitin or derivatives of same and cellulose ethers). Solvents or solutions are exemplified by Ringer's solution, water, distilled water, phosphate buffers, phosphate saline solutions, and other conventional fluids. Formulations of the type collyria, drops, etc. can also be prepared.

The invention can be used in mammals, particularly human beings. The results presented in the examples illustrate the efficacy of the invention for improving the viability of neurons subjected to conditions of excitotoxicity, particularly on retinal cultures, and describe the results of administrations in humans.

Detection, Diagnosis and Screening

Another object of the invention is based on a method for detecting a situation of neuronal stress or excitotoxicity in a subject, comprising measuring in vitro the expression of AKAP1, GABA(A)RAPL1 and/or PDE4 in a sample from the subject. Advantageously, the method comprises measuring the differential expression of the 3' non-coding region of the PDE4B gene and the rest of the gene, particularly the coding region.

Another object of the invention is therefore based on a method for detecting a situation of neuronal stress or excitotoxicity in a subject, comprising detecting the presence of a mutant form of RNA coding for AKAP1, GABA(A)RAPL1 and/or phosphodiesterase 4, particularly phosphodiesterase 4B, in particular a form in which all or part of the 3' non-coding region is deleted, in a sample from the subject.

Another object of the invention is based on the use of a nucleic acid comprising all or part of a sequence derived from the gene or messenger RNA coding for AKAPL1, GABA(A)RAPL1 or PDE4B for carrying out a method of diagnosis or detection of a situation of neuronal stress and more particularly the excitotoxicity situation.

In general, the invention is based on the use of a nucleic acid complementary to all or part of the gene or messenger coding for AKAP1, GABA(A)RAPL1 and/or PDE4B, for detecting pathological events of the type excitotoxicity, stress or neuron death, etc. More generally, the invention is based on a method for the diagnosis, screening, characterization or monitoring a degenerative ocular pathology, comprising demonstrating an alteration in the gene for PDE4 and/or AKAP1, GABA(A)RAPL1, or in the corresponding RNA.

The expression of AKAP1, GABA(A)RAPL1 and/or PDE4, or the differential expression, or the presence of an altered form can be determined by conventional molecular biology techniques, such as for instance sequencing, hybridization, amplification, RT-PCR, gel migration and the like. The invention can be used for the diagnosis or detection of different pathologies involving excitotoxicity phenomena, such as neurodegenerative ocular diseases (retinopathies, the retinal effects of glaucoma, age-related macular degeneration, etc.). It can be used for early detection, to demonstrate a predisposition, to guide the choice and adaptation of a treatment, to monitor the evolution of a pathology, and the like.

To carry out the genetic methods of diagnosis or detection according to the invention, one more particularly uses nucleic acids capable of revealing a deleted form of AKAP1, GABA(A)RAPL1 or PDE4B mRNA, in particular a form deleted of all or part of the 3' non-coding region of PDE4B. As a specific example, a nucleic acid is used which is complementary to all or part of the region comprised between residues 2760 to 2869 of Genbank sequence No. AF208023, or the corresponding residues of the sequence of the human PDE4B gene or mRNA. The cDNA sequence coding for human PDE4B is available in Genbank, No. NM_002600. The 3' non-coding region of the human PDE4B gene or RNA corresponds to residues 2461 to 4068 of Genbank sequence No. NM_002600.

In an advantageous manner, the nucleic acid which is used (as probe) comprises all or part of the sequence coding the 3' non-coding region of the PDE4B gene or RNA comprised between nucleotides 2384 and 2869 of Genbank sequence No. AF208023 or between nucleotides 2461 and 4068 of Genbank sequence No. NM_002600 or a sequence complementary to same.

According to particular embodiments, the invention uses a nucleic acid complementary to a region comprised in a following sequence:

residues 2384 to 2869 of Genbank sequence No. AF208023
residues 2500 to 2869 of Genbank sequence No. AF208023
residues 2760 to 2869 of Genbank sequence No. AF208023
residues 2780 to 2850 of Genbank sequence No. AF208023
residues 2790 to 2810 of Genbank sequence No. AF208023
residues 2600 to 4040 of Genbank sequence No. AF208023
residues 3000 to 4040 of Genbank sequence No. AF208023
residues 3500 to 4040 of Genbank sequence No. AF208023
residues 3900 to 4040 of Genbank sequence No. AF208023.

According to a particular embodiment, a nucleic acid is used which is complementary to the sequence of the region of PDE4 RNA resulting from the deletion of all or part of the 3' non-coding region. Deletion of a domain effectively creates new junctions in the sequence, which are specific of the deleted form and can be used to demonstrate the presence of such form in a sample.

Preferably, the probe and the target sequence have perfect complementary so as to ensure a better specificity of hybridization. Nevertheless, it is understood that some mismatches can be tolerated. The nucleic acid used for carrying out the hereinabove methods can be a DNA or an RNA, preferably a DNA of synthetic origin. It preferably contains from 10 to 500 bases, typically from 10 to 100 bases. It is understood that a longer nucleic acid may be used, if desired, although this is not preferred. Advantageously, the nucleic acid is a single-stranded DNA, from 10 to 500 bases, complementary at least to a region of the 3' non-coding sequence of PDE4B. The nucleic acid can be labelled, for example with a radioactive, enzymatic, luminescent, fluorescent, chemical label, and the like.

Another approach for detecting the presence of an alteration in the AKAP1, GABA(A)RAPL1 or PDE4 gene makes use of a primer or nucleic primer pair allowing selective amplification of a portion of AKAP1, GABA(A)RAPL1 or PDE4 RNA, preferably comprising a portion of the 3' non-coding region of PDE4 or coding region of AKAP1, GABA(A)RAPL1. Typically a primer is used which allows selective amplification of the altered form of AKAP1, GABA(A)RAPL1 or de PDE4 RNA, in particular a primer specific of the junction created by deleting a part of the RNA by splicing.

In this regard, an object of the invention is a primer complementary to part of AKAP1 RNA, and allowing amplification of a part of said RNA. The primer advantageously contains from 8 to 20 bases. Preferably it is composed of a fragment of 8 to 20 consecutive residues of Genbank sequence No. NM 009648, more preferably of at least a part of the region covered by nucleotides 1794 to 2322 of said sequence. In particular, said region contains an "RNA binding" domain of the KH family. Another object of the invention is based on a primer pair allowing specific amplification of at least a part of AKAP1 RNA, said pair comprising at least one primer such as defined hereinabove.

In this regard, an object of the invention is based on a primer complementary to a part of GABA(A)PL1 RNA, and allowing amplification of a part of said RNA. The primer advantageously contains from 8 to 20 bases. Preferably it is composed of a fragement of 8 to 20 consecutive residues of Genbank sequence No. BC 024706, more preferably of at least a part of the region covered by nucleotides 999 to 1400 of said sequence. Said region corresponds to the 3'UTR sequence of the RNA, involved in the stability and translationability of same.

To carry out the inventive methods, a biological sample from a subject, containing a nucleic acid, is contacted in vitro with a nucleic acid (probe, primer, etc.) such as defined hereinabove, and the formation of a hybrid or an amplification product is detected. The biological sample can be a sample of blood, fluid, cells, tissue, and the like. The nucleic acid can be immobilized on a support, of the type glass, silica, nylon, and the like.

The method of detection, screening or diagnosis can be carried out with different types of samples from a subject, such as for example tissue biopsies, particularly of nerve tissue. In a particularly surprising and advantageous manner, the present invention also shows that deregulation of PDE4 expression, correlated with the excitotoxicity phenomenon, can be directly demonstrated in muscle tissue.

Another object is based on a kit for analyzing the expression of PDE4, AKAP1 and/or GABA(A)RAPL1, the kit comprising a nucleotide probe specific of a part of the mRNA sequence of PDE4, AKAP1 and/or GABA(A)RAPL1.

Another object is based on a kit for analyzing the expression of AKAP1 and/or GABA(A)RAPL1, particularly the expression of altered forms of AKAP1 and/or GABA(A)RAPL1, the kit comprising a nucleotide primer pair allowing specific amplification of at least a part of a region of the mRNA of a specific isoform of AKAP1 and/or GABA(A)RAPL1.

Methods of Selection and Tools

Other objects of the invention relate to methods for the selection, identification or characterization of compounds active on pathologies related to excitotoxicity, or to neuronal stress, in particular on degenerative ocular pathologies, comprising contacting test compounds with a cell expressing PDE4B (in particular a variant deleted of the 3' non-coding region), AKAP1 and/or GABA(A)RAPL1, and identifying compounds inhibiting the expression or activity of said protein.

The methods can be carried out with different cell populations, such as primary cells or mammalian cell lines (human, murine, and the like). Advantageously, cells are used which do not naturally express PDE4B, AKAP1 and/or GABA(A)RAPL1, transfected with a nucleic acid encoding the desired variant. In this way, the selectivity of the method is enhanced. It is also possible to use lower eukaryotic cells (yeasts, etc.) or prokaryotic cells.

The screening methods can also be performed in an acellular system, by measuring the capacity of test compounds to bind PDE4B, AKAP1 and/or GABA(A)RAPL1 or a variant or fragment thereof.

Another object of the invention relates to any nucleic acid coding a polypeptide such as defined hereinabove, the vectors containing same, recombinant cells, and uses. The vectors can be plasmids, phages, cosmids, viruses, artificial chromosomes, etc. Examples of preferred vectors are plasmid vectors, such as those derived from commercially available plasmids (pUC, pcDNA, pBR, etc.). Such vectors advantageously contain a selection gene and/or an origin of replication and/or a transcriptional promoter. Other particular vectors are exemplified by viruses or phages, in particular replication-defective recombinant viruses, such as viruses derived from retrovirus, adenovirus, AAV, herpes virus, baculovirus, and the like. The vectors can be used in any competent host, such as prokaryotic or eukaryotic cells, for example. These may be bacterial (for example *E. coli*), yeasts (for example *Saccharomyces* or *Kluyveromyces*), plant cells, insect cells, mammalian cells, particularly human, etc. They may be cell lines, primary cells, mixed cultures, etc.

Other aspects and advantages of the invention will become apparent in the following examples, which are given for purposes of illustration and not by way of limitation.

By extension, all the uses described for AKAP1 and/or GABA(A)RAPL1 can be implemented for PBR and GABA(A) receptors.

LEGENDS OF FIGURES

Figure 1B:
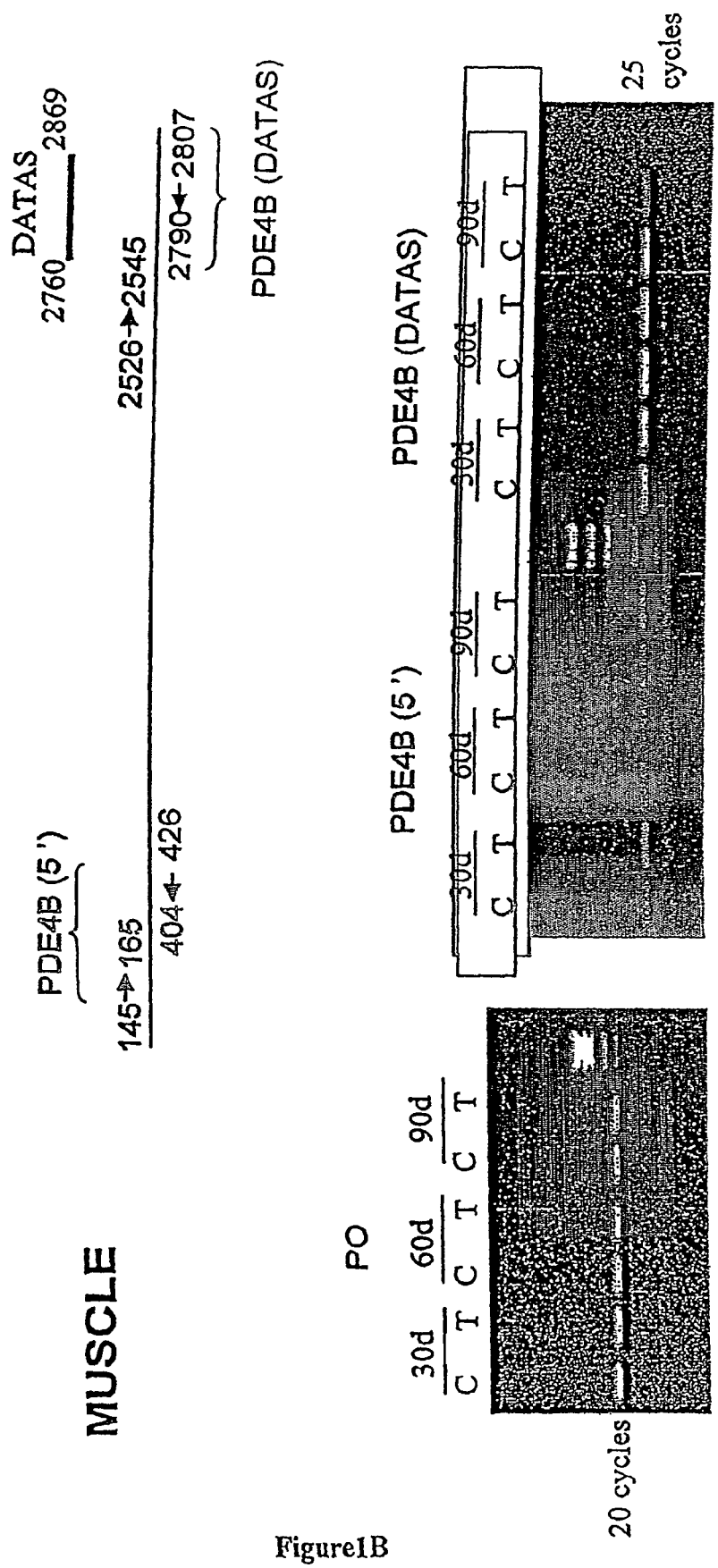

FIG. 1: Semi-quantitative PCR of PDE4B from brain (1A) and muscle (1B) samples.

Figure 2:
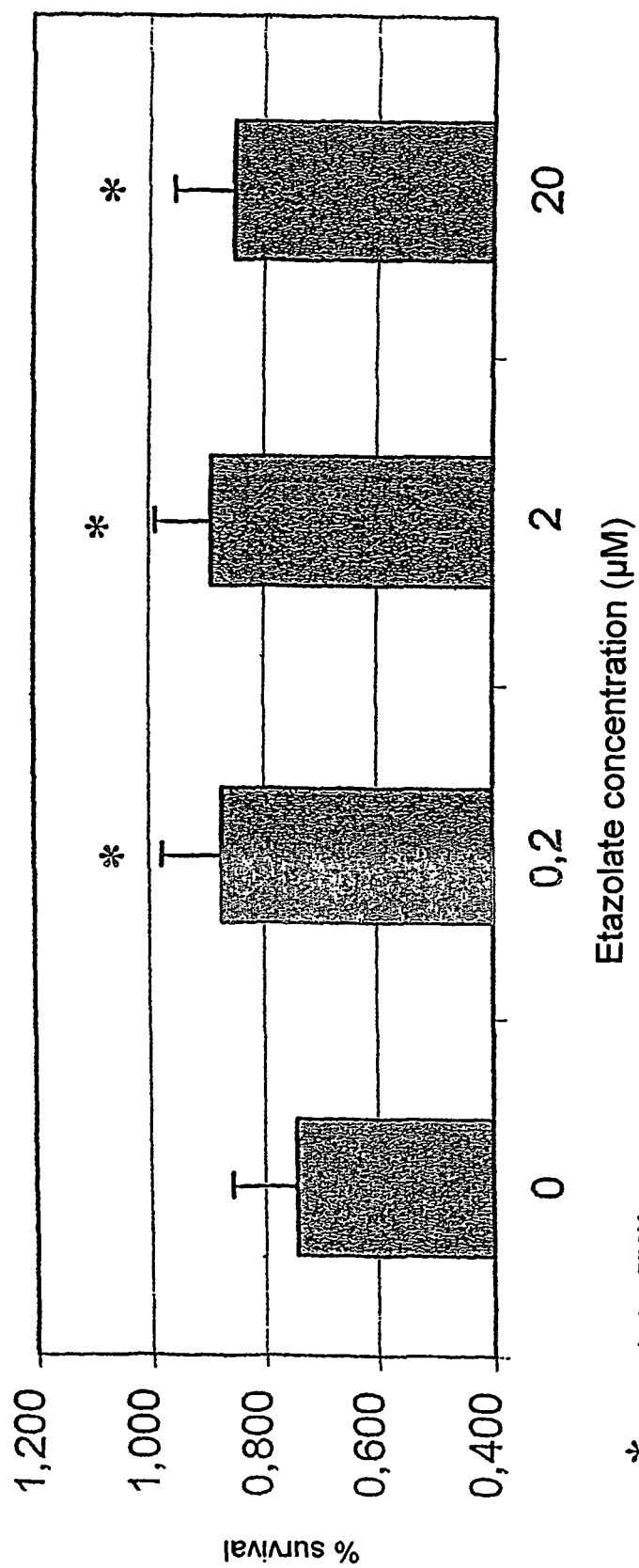

FIG. 2: Neuroprotective effect of etazolate on NMDA/serine-induced toxicity in cerebellar granular cells.

Figure 3:
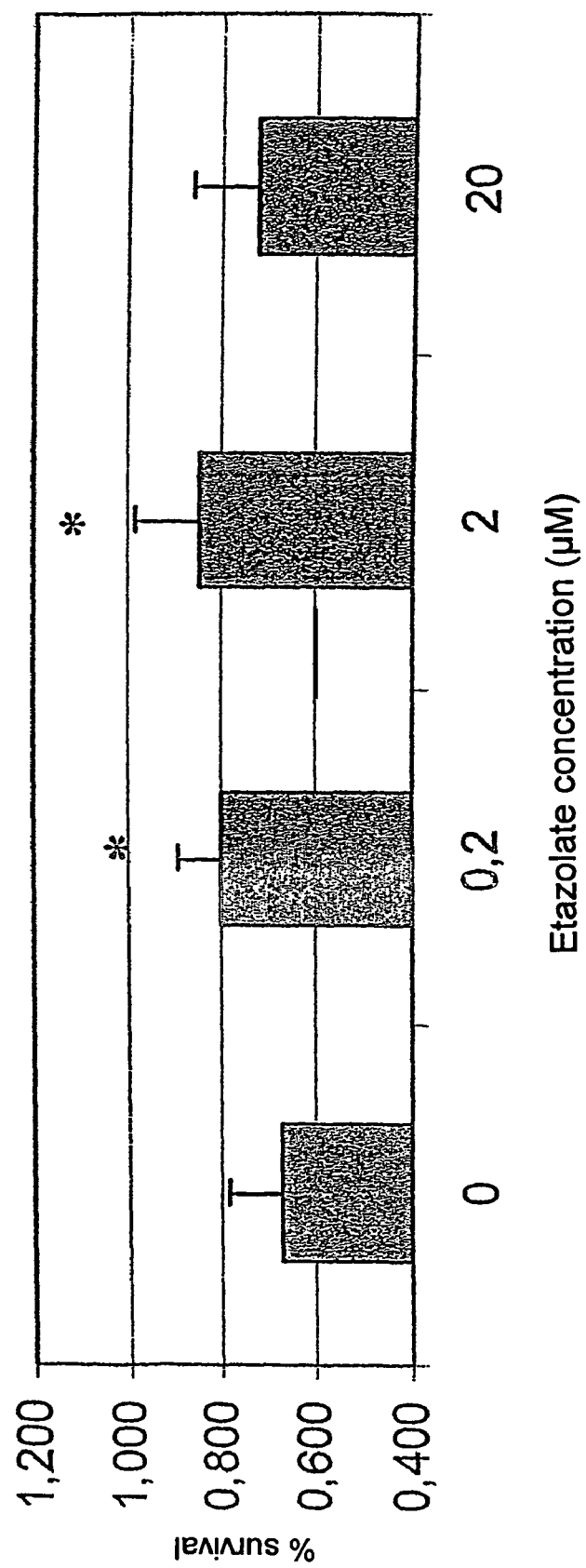

FIG. 3: Neuroprotective effect of etazolate on kainate-induced toxicity in cerebellar granular cells.

Figure 4:
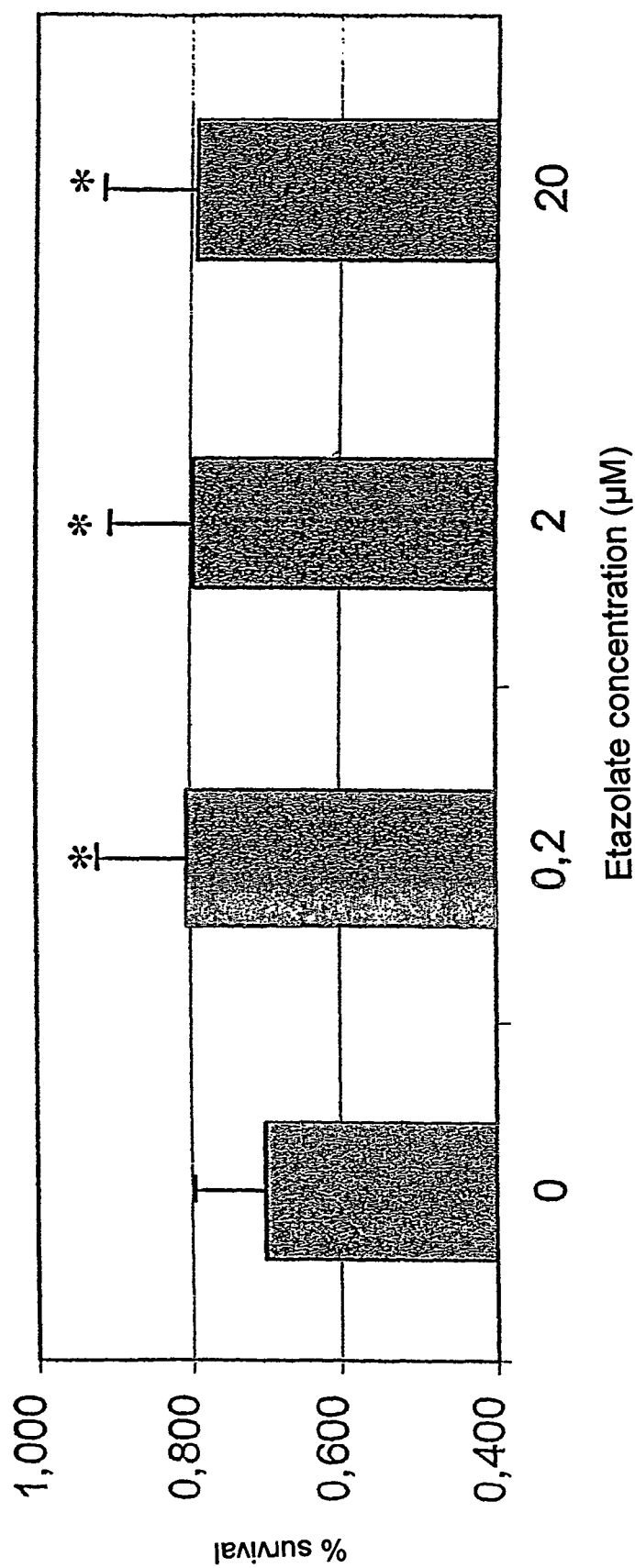

FIG. 4: Neuroprotective effect of etazolate on NMDA/serine-induced toxicity in cortical neurons.

Figure 5:
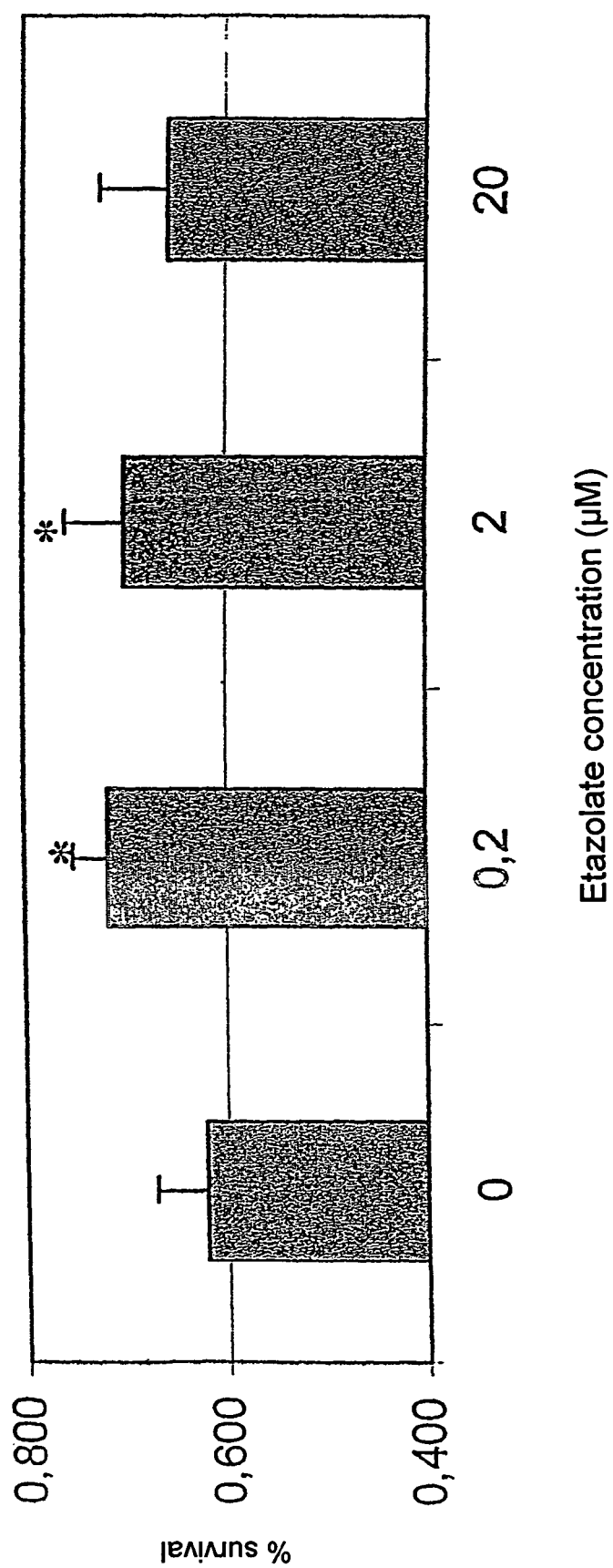

FIG. 5: Neuroprotective effect of etazolate on kainate-induced toxicity in cortical neurons.

Figure 6:
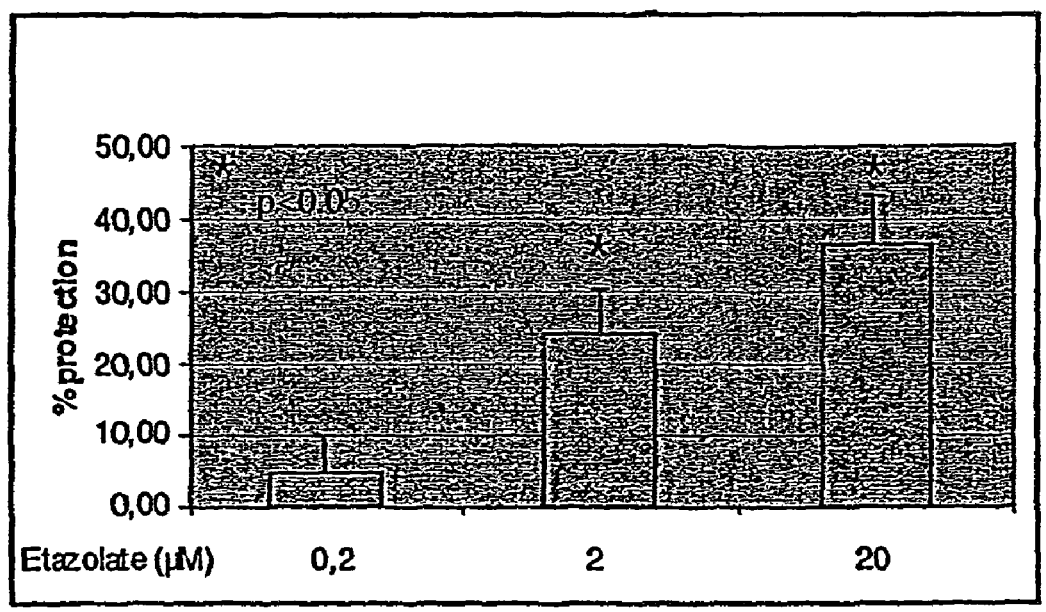

FIG. 6: Neuroprotective effect of etazolate on NMDA/serine-induced toxicity in ventral spinal cord cells.

Figure 7:
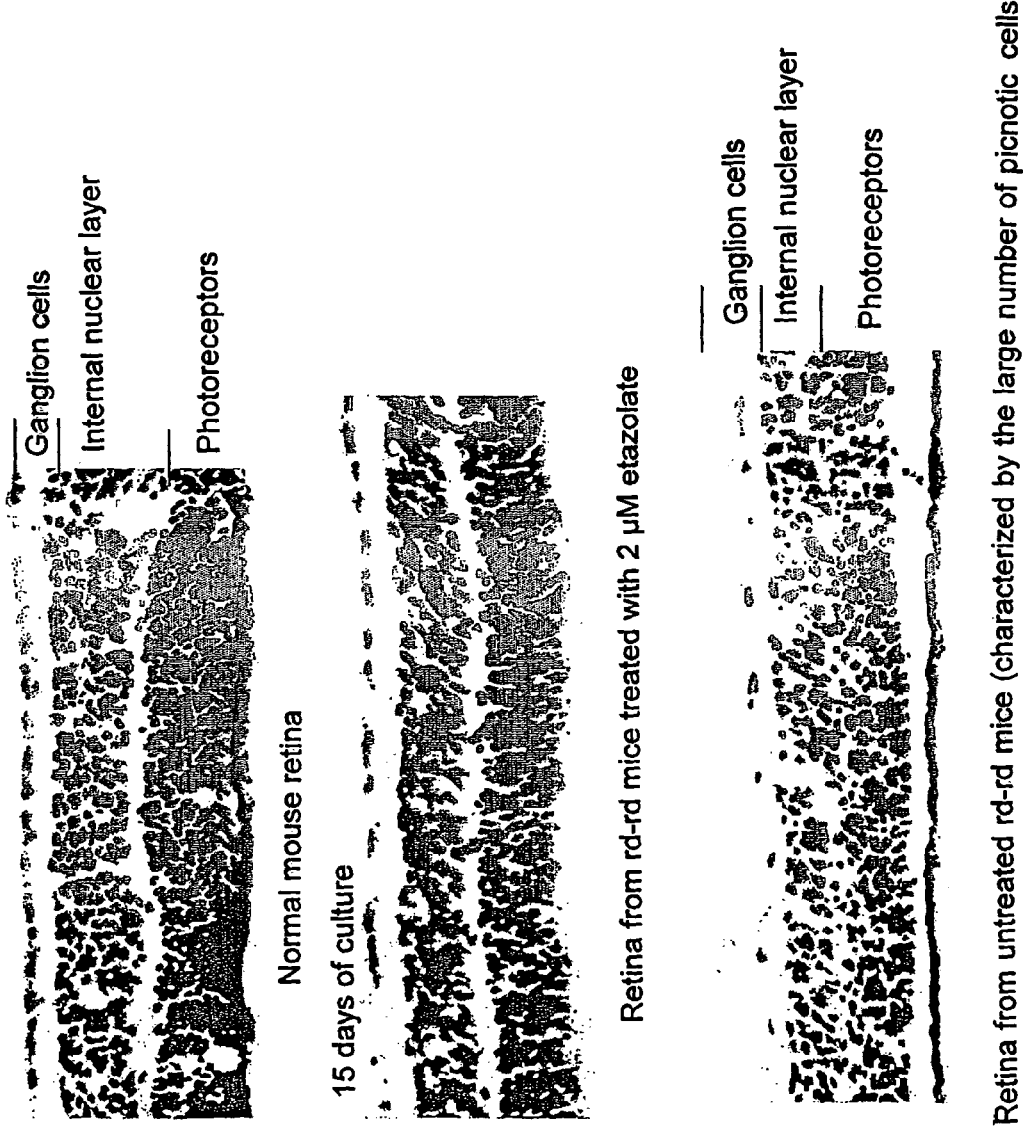

FIG. 7: Neuroprotective effect of etazolate in retina.

EXAMPLES

Example 1

Identification of PDE4. AKAP1 and/or GABA(A)RAPL1 as Molecular Targets of Excitotoxicity Qualitative differential analysis was carried out using polyadenylated RNA (poly A+) extracted from the brains of animals corresponding to different stages, without preliminary isolation of neurons so as to take into account a maximum of alternative splicing events related to development of the pathology. The poly A+ RNA were prepared according to methods known to those skilled in the art. In particular, this may be by means of a treatment with chaotropic agents like guanidium thiocyanate followed by extraction of total RNA with solvents (phenol, chloroform for example). Such methods are well known to those skilled in the art (see Maniatis et al., Chomczynsli et al., Anal. Biochem. 162 (1987) 156), and can be easily performed using commercially available kits. Poly A+ RNA was prepared from said total RNA, according to conventional methods known to those skilled in the art and provided in commercial kits. These poly A+ RNA served as matrix for reverse transcription reactions with the help of reverse transcriptase. Advantageously, reverse transcriptases devoid of RNase H activity are used which make it possible to obtain first complementary DNA strands which are larger than those yielded with conventional reverse transcriptases. Said Rnase H-free reverse transcriptase preparations are commercially available.

For each point in the time curve of disease development (30 days, 60 days and 90 days), poly A+ RNA and single stranded cDNA were prepared from transgenic animals (T) and syngeneic controls (C).

In accordance with the DATAS method, hybridizations of mRNA (C) with cDNA (T) and reciprocal hybridizations of mRNA (T) with cDNA (C) were done at each time point.

These mRNA/cDNA heteroduplexes were then purified according to the protocols of the DATAS method.

RNA sequences which did not pair with a complementary DNA were released from the heteroduplexes by the action of RNase H, as said enzyme degrades paired RNA sequences. These unpaired sequences represent the qualitative differences which exist between RNAs which otherwise are homologous to each other. Said qualitative differences can be located anywhere on the RNA sequence, either 5', 3' or inside the sequence and particularly in the coding sequence. Depending on their location, said sequences may not only be splicing modifications but may also result from translocations or deletions.

The RNA sequences representing qualitative differences were then cloned by methods known to those skilled in the art and in particular those described in the patent for the DATAS method.

These sequences were grouped into cDNA libraries which constitute qualitative differential libraries. One of said libraries contains exons and introns specific of the healthy situation; the other libraries contain splicing events characteristic of pathological conditions.

Differential expression of the clones was checked by hybridization with probes obtained by reverse transcription of messenger RNA extracted from the different situations under study. Clones displaying differential hybridization were retained for further analysis. The sequences identified by DATAS correspond to introns and/or exons differentially expressed by splicing between pathological situations and the healthy situation. Said splicing events can be specific of a given step in disease development or characteristic of the healthy state.

Comparison of these sequences with the data bases allows to classify the information obtained and propose a sensible selection of sequences based on their diagnostic or therapeutic interest.

Implementation of DATAS on RNA from 60-day-old control and transgenic animals led to the isolation of a cDNA fragment derived from phosphodiesterase 4B mRNA. Said fragment corresponds to an exon fragment specifically present in control animals and therefore specifically deleted in animals transgenic for SOD1 G93A at the 60-day stage. Said fragment encompasses nucleotides 377 to 486 numbered from the mouse PDE4B stop codon (GenBank sequence No. AF208023). Said sequence comprises 2912 bases, the deleted fragment corresponding to bases 2760 to 2869. This is a non-coding region which is differentially expressed between control and transgenic animals, due to the alternative use of a 3' non-coding exon or to the use of two alternative polyadenylation sites.

Implementation of DATAS on RNA from 60-day-old control and transgenic animals also led to the isolation of a cDNA fragment derived from AKAP1 mRNA. Said fragment corresponds to an exon fragment specifically present in control animals and therefore specifically deleted in animals transgenic for SOD1G93A at the 60-day stage. Said fragment is homologous to nucleotides 1794 to 2322 of GenBank sequence No. NM_009648. This is a coding region which is differentially expressed between control and transgenic animals, due to alternative splicing.

Implementation of DATAS on RNA from 60-day-old control and transgenic animals also led to the isolation of a cDNA fragment derived from GABA(A)RAPL1 mRNA. Said fragment corresponds to an exon fragment specifically present in control animals and therefore specifically deleted in animals transgenic for SOD1G93A at the 60-day stage. Said fragment is homologous to nucleotides 1055 to 1461 of GenBank sequence No. BC024706. This region is derived from the 3' non-coding region and is differentially expressed between control and transgenic animals.

Example 2

RT-PCR Experiments: Confirmation of Differential Expression

The differential expression of PDE4B in a situation of neuronal stress, versus a reference situation, was checked by RT-PCR experiments shown in FIG. 1. Said experiments were carried out according to methods well known to those skilled in the art and allowed monitoring of the expression of two distinct regions of PDE4B mRNA. One of said regions includes the initiation codon for this mRNA (PDE4B 5'), the other partly covers the fragment identified by DATAS (PDE4B DATAS). The locations of the PCR primers which were used are indicated in FIG. 1.

PO RNA is a ribosomal RNA used as internal control to check that the same amount of RNA was used for each experimental point. The analyses were performed on RNA extracted from control (C) and transgenic (T) animals aged 30, 60 and 90 days, that is, before appearance of pathological symptoms.

Total RNA from the brains of control SOD1 G93A mice aged 30, 60 and 90 days was transcribed to cDNA using the standard Superscript™ protocol (Invitrogen). For semi-quantitative PCR the products of the reverse transcription reaction were diluted 10-fold. Primers specific for the DATAS fragment corresponded for the sense nucleotide to nucleotides 2526-2545 (5' GCC AGG CCG TGA AGC AAA TA 3'; SEQ ID NO: 1), and for the antisense to 2790-2807 (5' TCA MG ACG CGA AAA CAT 3'; SEQ ID NO: 2) and for the more 3' fragment the primers corresponded for the sense nucleotide to nucleotides 145-165 (5' CCG CGT CAG TGC CTT TGC TAT 3'; SEQ ID NO: 3), and for the antisense to 426-404 (5' CGC TGT CGG ATG CTT TTA TTC AC 3'; SEQ ID NO: 4). PO was used as reference gene and was amplified by the following primers: sense: 5' TCG CTT TCT GGA GGG TGT $C_3$' (SEQ ID NO: 5) and antisense: CCG CAG GGG CAG CAG TGG 3' (SEQ ID NO:6).

Amplification was carried out by 30 PCR cycles as follows:

30 seconds at 94° C.

1 minute at 57° C.

30 seconds at 72° C., followed by one 2-minute cycle at 72° C.

The different PCR products were run on a 1.5% agarose gel. The experiment was repeated three times with two different reverse transcription reactions.

FIG. 1 shows the results obtained on RNA extracted from brain or muscle of the animals.

While the same amount of cDNA was amplified from PO RNA in all the samples, variations were seen for PDE4B mRNA; the most significant variations were found in 90-day-old animals: while expression of the PDE4 5' fragment was increased in the brains of transgenic animals, the expression of PDE4B (DATAS) was very sharply decreased.

This result establishes a correlation between the decrease in expression of a 3' non-coding fragment of PDE4B mRNA and the increase in expression of the 5' coding region of this same messenger. This finding is altogether compatible with the presence of mRNA destabilization sequences in the sequence identified by DATAS and demonstrates the correlation between PDE4B expression and the phenomenon of excitotoxicity.

Example 3

Inhibition of Excitotoxity by PBR Ligands Which are PDE4 Inhibitors

In this example, cerebellar granular neurons, cortical neurons and ventral spinal cord cells from rats were cultured according to methods known to those skilled in the art.

Primary Culture of Cerebellar Granular Cells:

Seven-day-old Wistar rats were decapitated and brains were dissected. The meninges were removed and the tissue was then cut into small pieces and trypsinized for 15 minutes at 37° C. Cells were dissociated by trituration, then placed in culture at a density of 300,000 cells per $cm^2$ in Eagle basic medium supplemented with 10% fetal calf serum and 2 mM glutamine. The next day, 10 µM ARA-C, an antimitotic agent, was added to prevent proliferation of glial cells. The cells were treated on day 9 of culture with the inhibitor compound etazolate, three hours before adding the toxic agents 50 µM kainate or 100 µM N-methyl-D-aspartate in the presence of 10 µM D-serine. Immediately before adding the toxic agents, 8-bromo-cAMP was added. All treatments were done at least in duplicate and in at least two different cultures. After a 6-hour incubation, toxicity was measured by the MTT test. The results were normalized to the untreated mean and analyzed statistically with a Wilcoxon test. The level of significance was $p \leq 0.05$.

Primary Cultures of Cortical Cells:

Wistar rat embryos aged 16 days were removed and the cortex dissected. After trypsination at 37° C. for 25 minutes, the cells were dissociated by trituration, then seeded in minimum essential medium supplemented with 10% horse serum, 10% fetal calf serum and 2 mM glutamine, at a density of 300,000 cells per $cm^2$. After 4 days of culture, half the medium was replaced with minimum essential medium supplemented with 5% horse serum and 2 mM glutamine. The same day, the antimitotic 5-fluoro-2-deoxyuridine (10 µM) was added. After 7 and 11 days of culture, half the medium was replaced with conditioned medium composed of MEM supplemented with 5% horse serum and 2 mM glutamine; prior to use this medium was passed overnight on a layer of cortical astrocytes. On day 14, the cells were treated with the inhibitor compound etazolate, 1 hour before adding the toxic agents 50 µM kainate or 20 µM N-methyl-D-aspartate in the presence of 10 µM D-serine. All treatments were done at least in duplicate and in at least two different cultures. After a 6-hour incubation, toxicity was measured by the MTT test. The results were normalized to the untreated mean and analyzed statistically with a Wilcoxon test. The level of significance was $p \leq 0.05$.

Primary Cultures of Ventral Spinal Cord Cells:

Cells were isolated from 14-day-old Wistar rat embryos. On arrival, gestating rats were sacrificed by carbon dioxide intoxication.

The chain of embryos was removed and placed in a dish containing PBS.

The spinal cord of each embryo was dissected and the ventral cord was separated from the dorsal cords. The ventral cords were then trypsinized at 37° C. for 20 minutes. Trypsinization was stopped by addition of Leibovitz 15 medium, 20% horse serum, supplement N2 (1×), 20% glucose (3.2 mg/ml), 7.5% bicarbonate (1.8 mg/ml) and 2 mM L-glutamine. The cells were dissociated by trituration. Clumps of tissue were removed and the dissociated cells were then quantified by trypan blue staining. The cells were seeded at 250,000 cells per $cm^2$ in neurobasal medium containing 2% horse serum, supplement B27 (1×), and 2 mM glutamine. After 3 days of culture in vitro, the antimitotic agent ARA-C (5 µM) was added to the cells to inhibit production of glial cells. The cells were cultured at 37° C. in a humidified incubator (5% $CO_2$) for 9 days, after which they were treated with the inhibitor compound etazolate, 3 hours and 1 hour, respectively, before adding the toxic agents 50 µM kainate or 100 µM N-methyl-D-aspartate (NMDA) in the presence of 10 µM D-serine. All treatments were done at least in duplicate and in at least two different cultures. After a 3-hour incubation with NMDA/D-serine as toxic agent and a 1-hour incubation with kainate, toxicity was measured by the MTT test. The results were normalized to the untreated mean and analyzed statistically with a Wilcoxon test with $p < 0.05$.

MTT:

Toxicity was measured with the MTT test. After incubation with the compounds, MTT was added at 0.5 mg/ml final concentration per well. The plates were then incubated in the dark for 30 minutes at 37° C. The medium was aspirated and the crystals resuspended in 500 µl of DMSO (dimethylsulfoxide). Absorbance at 550 nm was measured and the percentage viability was calculated.

Results:

The results obtained are presented in FIGS. 2 to 6. They illustrate the protective effect of the inventive compounds on neuron survival. After co-treatment of neurons with an inhibitor compound of the invention, a dose-related protective effect was seen in two models of excitotoxicity induction (NMDA/serine and kainate).

FIGS. 2 and 3 present the results obtained with etazolate on cerebellar granular cells. They show that etazolate afforded a 60% protective effect on these cells in the case of NMDA/serine treatment, and 57% in the case of kainate-induced toxicity.

FIGS. 4 and 5 present the results obtained with etazolate on cortical neurons. They show that etazolate afforded a 33% protective effect on these cells in the case of NMDA/serine treatment, and 25% in the case of kainate-induced toxicity.

FIG. 6 presents the results obtained with etazolate on ventral spinal cord cells. They show that etazolate afforded a 36% protective effect on these cells in the case of NMDA/serine treatment.

Thus, the invention not only demonstrates the involvement of PDE4B, PBR and GABA(A) receptors in excitotoxicity mechanisms, but also the capacity of inhibitors and ligands to preserve neuron viability during excitotoxic stress.

Example 4

In vitro Experiments on Retinal Cultures

This example describes the effects of a PDE4 inhibitor on retina of rd1 mice, which are characterized by a loss of visual cells starting two weeks after birth.

For each etazolate concentration (0.02 µM, 0.2 µM, 2 µM and 20 µM), six retinal explants from rd1 mice were cultured for 21 days. The culture was started on postnatal day 7 in medium free of bovine fetal serum but containing etazolate at the indicated concentration. Six retinal explants from the same animals were used as controls for the treated explants. In this case, the explants were grown in culture medium alone or in culture medium containing the vehicle used for etazolate. For both conditions (control and treatment), the culture medium was changed every two days. After 21 days of culture, the explants were fixed, sectioned and labelled for histopathologic studies.

Explants from untreated rd1 mice (postnatal day 28) lost most of their photoreceptors in culture, and the presence of an increase in photoreceptors was then detected by counting the remaining photoreceptors.

Results

The results obtained with 2 µM etazolate show that the photoreceptors of rd1 mice treated with etazolate were better preserved thatn those of untreated rd-rd mice. As shown in FIG. 7, untreated rd-rd mice displayed the following characteristics: a high number of picnotic cells and a decrease in the number of photoreceptor nuclei. In contrast, in etazolate-treated explants, the photoreceptor layer was much better preserved and resembled that seen in non-transgenic mice. These explants were also characterized by a marked reduction in the number of picnotic cells as compared with explants from untreated rd-rd mice.

Example 5

Effect of Etazolate on the PBR

To demonstrate this effect, the experiments were conducted in HeLa cells, which have been shown to express the PBR. The PBR is situated between the inner and outer mitochondrial membrane. It forms part of the transition pore complex, which participates in regulating mitochondrial flux by opening the mitochondrial pore. There exist molecules which display high affinity for PBR, particularly Ro5-4864 and PK11195.

By monitoring mitochondrial-specific fluorescence of rhodamine 1,2,3, the effects of PBR-specific ligands and those of etazolate could be followed.

The results show that etazolate induced the same loss of fluorescence as the PBR-specific ligands Ro5-4864 and PK11195.

Etazolate therefore appears to be a PBR ligand which protects neurons from death during excitotoxic phenomena.

Example 6

Clinical Use in Humans

This example describes the conditions for clinical use of etazolate in the treatment of neurodegenerative diseases. It illustrates the therapeutic potential of the invention and the conditions of use thereof in humans.

In this study, increasing doses of etazolate (0.5, 1, 2, 5, 10 and 20 mg) were administered orally in the form of 0.5 and 5 mg capsules to different and sequential groups of eight young healthy male volunteers. This was a single-center, double-blind study in which two of the eight subjects received a placebo.

The following parameters were evaluated: clinical tolerability (adverse effects, clinical signs, changes in blood pressure or heart rate), electrocardiographic tolerability (recording of the ECG) and biological tolerability (hematology and blood biochemistry, urinalysis) for 24 hours after dosing. The product was assayed in plasma at different times before and after administration in each subject (0.25-0.50-1.00-1.50-2.00-3.00-4.00-5.00-6.00-8.00-10.00-12.00 and 24.00 hours). The product was also assayed in urine collected before and after administration (4, 4-8,8-12 and 12-24 hours).

At the end of the dose escalation phase, an additional group of six subjects was given etazolate at two different times: after fasting and with a high fat meal. This second phase aimed to compare the variations in blood levels of the product between the two dosing conditions. The following parameters were evaluated: clinical tolerability (adverse effects, clinical signs, changes in blood pressure or heart rate), electrocardiographic tolerability (recording of the ECG) and biological tolerability (hematology and blood biochemistry, urinalysis) for 24 hours after dosing. The product was assayed in plasma at different times before and after administration in each subject (0.25-0.50-1.00-1.50-2.00-3.00-4.00-5.00-6.00-8.00-10.00-12.00 and 24.00 hours). The product was also assayed in urine collected before and after administration (4, 4-8,8-12 and 12-24 hours). A gastroresistant capsule has also been formulated for this product for human clinical trial use.

The results from the first escalating dose phase of the study show that etazolate was well tolerated and did not cause any side effects. Moreover, the plasma assays confirmed that absorption of the product in humans is good at high doses.

Together, these results demonstrate that the inventive compounds have outstanding properties on survival of neurons, in particular retinal, and can be administered to humans without side effects. These results therefore allow the development of novel, effective therapeutic approaches for human neurodegenerative ocular diseases.

The invention claim is:

1. A method for treating age-related macular degeneration in a subject in need of said treating, the method comprising administering to the subject an effective amount of etazolate.

2. The method of claim 1, wherein said treating increases neuron survival in said subject.

3. A method of claim 1, wherein etazolate is administered in oral form.

* * * * *